United States Patent
Esnouf

(10) Patent No.: US 9,528,897 B2
(45) Date of Patent: Dec. 27, 2016

(54) PRESSURE INDICATOR

(75) Inventor: Philip Stuart Esnouf, Victoria (AU)

(73) Assignee: CHIMDEN MEDICAL PTY LTD, Richmond, Victoria (AU)

( * ) Notice: Subject to any disclaimer, the term of this patent is extended or adjusted under 35 U.S.C. 154(b) by 742 days.

(21) Appl. No.: 13/388,864

(22) PCT Filed: Aug. 11, 2010

(86) PCT No.: PCT/AU2010/001024
§ 371 (c)(1),
(2), (4) Date: Apr. 16, 2012

(87) PCT Pub. No.: WO2011/017756
PCT Pub. Date: Feb. 17, 2011

(65) Prior Publication Data
US 2012/0186510 A1    Jul. 26, 2012

(30) Foreign Application Priority Data

Aug. 13, 2009  (AU) ................................ 2009903814
Mar. 23, 2010  (AU) ................................ 2010901240

(51) Int. Cl.
*G01L 19/14*    (2006.01)

(52) U.S. Cl.
CPC .................................... *G01L 19/144* (2013.01)

(58) Field of Classification Search
CPC ............ G01L 7/08; G01L 7/082; G01L 7/084; G01L 7/088; G01L 7/104
USPC .......... 116/266, 268, 270, 271, 284; 73/708, 73/715, 729.1, 729.2, 730, 731; 128/205.23; 600/488; D10/85
See application file for complete search history.

(56) References Cited

U.S. PATENT DOCUMENTS

| | | | |
|---|---|---|---|
| 2,099,127 A | 11/1937 | Leech |
| 2,252,874 A | 8/1941 | Vischer |
| 2,839,788 A | 6/1958 | Dembiak |
| 2,862,498 A | 12/1958 | Weekes |
| 3,529,596 A | 9/1970 | Garner |
| 3,554,673 A | 1/1971 | Schwartz, Et Al. |

(Continued)

FOREIGN PATENT DOCUMENTS

| | | | |
|---|---|---|---|
| AU | 2004-260-552 A1 | 2/2005 |
| CA | 2012750 | 9/1990 |

(Continued)

OTHER PUBLICATIONS

International Search Report in PCT/AU2010/001024 dated Oct. 11, 2010.

(Continued)

*Primary Examiner* — Laura Martin
*Assistant Examiner* — Irving A Campbell
(74) *Attorney, Agent, or Firm* — Foley & Lardner LLP

(57) ABSTRACT

A pressure indicator: a body having a pressure chamber which has an inlet for communication with a fluid; a resilient diaphragm having a periphery sealed against the body and having one side thereof exposed to the fluid within the chamber; an indicating arm having an inner end which is integrally formed with the other side of the diaphragm and an outer end arm which is adjacent to a scale, the arrangement being such that pressure of the fluid within the chamber causes resilient deformation of the diaphragm which in turn causes the outer end of the arm to move relative to the scale thereby indicating the pressure of the fluid in the chamber.

21 Claims, 12 Drawing Sheets

(56) References Cited

U.S. PATENT DOCUMENTS

| | | | |
|---|---|---|---|
| 3,683,908 A | 8/1972 | Michael et al. | |
| 3,794,036 A | 2/1974 | Carroll | |
| 3,931,822 A | 1/1976 | Marici | |
| 4,056,104 A | 11/1977 | Jaffe | |
| 4,067,329 A | 1/1978 | Winicki et al. | |
| 4,096,759 A | 6/1978 | Desor | |
| 4,104,357 A | 8/1978 | Blair | |
| 4,116,201 A | 9/1978 | Shah | |
| 4,134,407 A | 1/1979 | Elam | |
| 4,159,722 A | 7/1979 | Walker | |
| 4,178,938 A | 12/1979 | Au et al. | |
| 4,178,940 A | 12/1979 | Au et al. | |
| 4,231,365 A | 11/1980 | Scarberry | |
| 4,256,099 A | 3/1981 | Dryden | |
| 4,285,340 A | 8/1981 | Gezari et al. | |
| 4,351,330 A | 9/1982 | Scarberry | |
| 4,445,366 A * | 5/1984 | Gray | 73/64.46 |
| 4,446,864 A | 5/1984 | Watson et al. | |
| 4,453,545 A | 6/1984 | Inoue | |
| 4,471,775 A | 9/1984 | Clair et al. | |
| 4,501,273 A | 2/1985 | McGinnis | |
| 4,509,514 A | 4/1985 | Brain et al. | |
| 4,510,273 A | 4/1985 | Miura et al. | |
| 4,526,196 A | 7/1985 | Pistillo | |
| 4,553,540 A | 11/1985 | Straith | |
| 4,583,917 A | 4/1986 | Shah | |
| 4,617,015 A * | 10/1986 | Foltz | 604/100.01 |
| 4,630,606 A | 12/1986 | Weerda et al. | |
| 4,654,643 A * | 3/1987 | Meisenheimer, Jr. | 340/626 |
| 4,689,041 A | 8/1987 | Corday et al. | |
| 4,700,700 A | 10/1987 | Eliachar | |
| 4,770,170 A | 9/1988 | Sato et al. | |
| 4,793,327 A | 12/1988 | Frankel | |
| 4,798,597 A | 1/1989 | Vaillancourt | |
| 4,809,589 A * | 3/1989 | Bertrand | 92/98 R |
| 4,825,862 A | 5/1989 | Sato et al. | |
| 4,832,020 A | 5/1989 | Augustine | |
| 4,850,349 A | 7/1989 | Farahany | |
| 4,856,510 A | 8/1989 | Kowalewski et al. | |
| 4,872,483 A | 10/1989 | Shah | |
| 4,924,862 A | 5/1990 | Levinson | |
| 4,953,547 A | 9/1990 | Poole, Jr. | |
| 4,972,963 A | 11/1990 | Guarriello et al. | |
| 4,981,470 A | 1/1991 | Bombeck, IV | |
| 4,995,388 A | 2/1991 | Brain | |
| 5,038,766 A | 8/1991 | Parker | |
| 5,042,469 A | 8/1991 | Augustine | |
| 5,042,476 A | 8/1991 | Smith | |
| 5,060,647 A | 10/1991 | Alessi | |
| 5,067,496 A | 11/1991 | Eisele | |
| 5,174,283 A | 12/1992 | Parker | |
| 5,203,320 A | 4/1993 | Augustine | |
| 5,218,970 A | 6/1993 | Turnbull et al. | |
| 5,235,973 A | 8/1993 | Levinson | |
| 5,241,325 A | 8/1993 | Nguyen et al. | |
| 5,241,956 A | 9/1993 | Brain et al. | |
| 5,249,571 A | 10/1993 | Brain et al. | |
| 5,273,537 A | 12/1993 | Haskvitz et al. | |
| 5,277,178 A | 1/1994 | Dingley et al. | |
| 5,282,464 A | 2/1994 | Brain et al. | |
| 5,297,547 A | 3/1994 | Brain et al. | |
| 5,303,697 A | 4/1994 | Brain et al. | |
| 5,305,743 A | 4/1994 | Brain | |
| 5,311,861 A | 5/1994 | Miller et al. | |
| 5,331,967 A | 7/1994 | Akerson et al. | |
| 5,339,805 A | 8/1994 | Parker | |
| 5,339,808 A | 8/1994 | Don Michael | |
| 5,355,879 A | 10/1994 | Brain et al. | |
| 5,361,753 A | 11/1994 | Pothmann et al. | |
| 5,391,248 A | 2/1995 | Brain | |
| 5,400,771 A | 3/1995 | Pirak et al. | |
| 5,421,325 A | 6/1995 | Cinberg et al. | |
| 5,438,982 A | 8/1995 | MacIntyre | |
| 5,443,063 A | 8/1995 | Greenberg | |
| 5,452,715 A | 9/1995 | Boussignac | |
| 5,459,700 A | 10/1995 | Jacobs | |
| 5,487,383 A | 1/1996 | Levinson | |
| 5,529,582 A | 6/1996 | Fukuhara | |
| 5,546,935 A | 8/1996 | Champeau | |
| 5,546,936 A | 8/1996 | Virag et al. | |
| 5,551,420 A | 9/1996 | Lurie et al. | |
| 5,554,673 A | 9/1996 | Shah | |
| 5,569,219 A | 10/1996 | Hakki et al. | |
| 5,577,693 A | 11/1996 | Corn | |
| 5,582,167 A | 12/1996 | Joseph | |
| 5,584,290 A | 12/1996 | Brain | |
| 5,599,301 A | 2/1997 | Jacobs et al. | |
| 5,623,921 A | 4/1997 | Kinsinger et al. | |
| 5,626,151 A | 5/1997 | Linden | |
| 5,632,271 A | 5/1997 | Brain et al. | |
| RE35,531 E | 6/1997 | Callaghan et al. | |
| 5,653,229 A | 8/1997 | Greenberg | |
| 5,655,528 A | 8/1997 | Pagan et al. | |
| 5,682,880 A | 11/1997 | Brain et al. | |
| 5,692,498 A | 12/1997 | Lurie et al. | |
| 5,694,929 A | 12/1997 | Christopher | |
| 5,711,293 A | 1/1998 | Brain et al. | |
| 5,738,094 A | 4/1998 | Hoftman | |
| 5,743,254 A | 4/1998 | Parker | |
| 5,743,258 A | 4/1998 | Sato et al. | |
| 5,746,202 A | 5/1998 | Pagan et al. | |
| 5,771,889 A | 6/1998 | Pagan et al. | |
| 5,778,872 A | 7/1998 | Fukunaga et al. | |
| 5,791,341 A | 8/1998 | Bullard | |
| 5,794,617 A | 8/1998 | Brunell et al. | |
| 5,816,240 A | 10/1998 | Komesaroff | |
| 5,819,723 A | 10/1998 | Joseph | |
| 5,832,916 A | 11/1998 | Lundberg et al. | |
| 5,850,832 A | 12/1998 | Chu | |
| 5,855,203 A | 1/1999 | Matter | |
| 5,856,510 A | 1/1999 | Meng et al. | |
| 5,860,418 A | 1/1999 | Lundberg et al. | |
| 5,865,176 A | 2/1999 | O'Neil et al. | |
| 5,878,745 A | 3/1999 | Brain et al. | |
| 5,881,726 A | 3/1999 | Neame | |
| 5,893,891 A | 4/1999 | Zahedi et al. | |
| 5,896,858 A | 4/1999 | Brain | |
| 5,915,383 A | 6/1999 | Pagan | |
| 5,921,239 A | 7/1999 | McCall et al. | |
| 5,924,862 A | 7/1999 | White | |
| 5,935,084 A | 8/1999 | Southworth | |
| 5,937,860 A | 8/1999 | Cook | |
| 5,957,133 A | 9/1999 | Hart | |
| 5,979,445 A | 11/1999 | Neame et al. | |
| 5,983,891 A | 11/1999 | Fukunaga | |
| 5,983,896 A | 11/1999 | Fukunaga et al. | |
| 5,983,897 A | 11/1999 | Pagan | |
| 5,988,167 A | 11/1999 | Kamen | |
| 5,996,582 A | 12/1999 | Turnbull | |
| 6,003,510 A | 12/1999 | Anunta | |
| 6,003,511 A | 12/1999 | Fukunaga et al. | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,062,219 A | 5/2000 | Lurie et al. | |
| 6,070,581 A | 6/2000 | Augustine et al. | |
| 6,079,409 A | 6/2000 | Brain | |
| D429,811 S | 8/2000 | Bermudez et al. | |
| 6,095,144 A | 8/2000 | Pagan | |
| 6,098,621 A | 8/2000 | Esnouf | |
| 6,110,143 A | 8/2000 | Kamen | |
| 6,116,243 A | 9/2000 | Pagan | |
| 6,119,695 A | 9/2000 | Augustin et al. | |
| 6,131,571 A | 10/2000 | Lampotang et al. | |
| 6,149,603 A | 11/2000 | Parker | |
| 6,155,257 A | 12/2000 | Lurie et al. | |
| 6,213,120 B1 | 4/2001 | Block et al. | |
| 6,224,562 B1 | 5/2001 | Lurie et al. | |
| 6,234,985 B1 | 5/2001 | Lurie et al. | |
| 6,240,922 B1 | 6/2001 | Pagan | |
| 6,251,093 B1 | 6/2001 | Valley et al. | |
| 6,269,813 B1 | 8/2001 | Fitzgerald et al. | |
| 6,315,739 B1 | 11/2001 | Merilainen et al. | |

(56) References Cited

U.S. PATENT DOCUMENTS

| | | |
|---|---|---|
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,511,922 B2 | 1/2003 | Krishnaraj et al. |
| 6,546,931 B2 | 4/2003 | Lin et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 6,737,345 B1 | 5/2004 | Lin et al. |
| 6,766,801 B1 | 7/2004 | Wright |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| 7,383,736 B2 | 6/2008 | Esnouf |
| 7,566,658 B2 | 7/2009 | Keum |
| 8,013,423 B2 | 9/2011 | Keum |
| 8,033,176 B2 | 10/2011 | Esnouf |
| 8,358,011 B1 | 1/2013 | Colburn et al. |
| 2003/0000534 A1 | 1/2003 | Alfery |
| 2003/0037790 A1 | 2/2003 | Brain |
| 2003/0051734 A1 | 3/2003 | Brain |
| 2003/0101998 A1 | 6/2003 | Zocca et al. |
| 2003/0131845 A1 | 7/2003 | Lin |
| 2003/0172925 A1 | 9/2003 | Zocca et al. |
| 2003/0172935 A1 | 9/2003 | Miller |
| 2004/0020491 A1 | 2/2004 | Fortuna |
| 2005/0081861 A1 | 4/2005 | Nasir |
| 2005/0139220 A1 | 6/2005 | Christopher |
| 2005/0178388 A1 | 8/2005 | Kuo |
| 2005/0274383 A1 | 12/2005 | Brain |
| 2006/0124132 A1 | 6/2006 | Brain |
| 2006/0201516 A1 | 9/2006 | Petersen et al. |
| 2006/0254596 A1 | 11/2006 | Brain |
| 2007/0240722 A1 | 10/2007 | Kessler |
| 2008/0048332 A1 | 2/2008 | Park |
| 2008/0142017 A1 | 6/2008 | Brain |
| 2008/0173981 A1 | 7/2008 | Chinthakindi et al. |
| 2009/0102052 A1 | 4/2009 | Ryu |
| 2009/0139524 A1 | 6/2009 | Esnouf |
| 2009/0212439 A1 | 8/2009 | Farooq et al. |
| 2009/0261475 A1 | 10/2009 | Keum |
| 2010/0216123 A1 | 8/2010 | Hirai et al. |
| 2011/0024866 A1 | 2/2011 | Tseng et al. |
| 2011/0256546 A1 | 10/2011 | Morris et al. |
| 2011/0281432 A1 | 11/2011 | Farooq et al. |
| 2012/0174929 A1 | 7/2012 | Esnouf |
| 2012/0186510 A1 | 7/2012 | Esnouf |
| 2014/0034060 A1 | 2/2014 | Esnouf et al. |

FOREIGN PATENT DOCUMENTS

| | | |
|---|---|---|
| CA | 2067782 | 5/1991 |
| CA | 2141167 | 7/1995 |
| DE | 4447186 A1 | 7/1996 |
| DE | 100 42 172 A1 | 4/2001 |
| EP | 0 389 272 A2 | 9/1990 |
| EP | 0 402 872 A1 | 12/1990 |
| EP | 0 294 200 B1 | 4/1992 |
| EP | 0 580 385 A1 | 1/1994 |
| EP | 0 712 638 A1 | 5/1996 |
| EP | 0 732 116 A2 | 9/1996 |
| EP | 0 796 631 A2 | 9/1997 |
| EP | 0 842 672 A2 | 5/1998 |
| EP | 0 845 276 A2 | 6/1998 |
| EP | 0 865 798 A2 | 9/1998 |
| EP | 0 922 465 A2 | 6/1999 |
| EP | 0 935 971 A2 | 8/1999 |
| EP | 1 119 386 B1 | 8/2001 |
| EP | 1 125 595 A1 | 8/2001 |
| EP | 1 800 706 A1 | 6/2007 |
| GB | 1 529 190 | 10/1978 |
| GB | 2 111 394 A | 7/1983 |
| GB | 2 205 499 A | 12/1988 |
| GB | 2 298 797 A | 9/1996 |
| GB | 2 317 342 A | 3/1998 |
| GB | 2 317 830 A | 4/1998 |
| GB | 2 318 735 A | 5/1998 |
| GB | 2 319 478 A | 5/1998 |
| GB | 2 321 854 A | 8/1998 |
| GB | 2 323 289 A | 9/1998 |
| GB | 2 323 290 A | 9/1998 |
| GB | 2 323 291 A | 9/1998 |
| GB | 2 323 292 A | 9/1998 |
| GB | 2 324 737 A | 11/1998 |
| GB | 2 359 996 A | 9/2001 |
| GB | 2 371 990 A | 8/2002 |
| GB | 2 405 588 A | 3/2005 |
| JP | H03-39169 A | 2/1991 |
| JP | H10-118182 A | 5/1998 |
| JP | H10-216233 A | 8/1998 |
| JP | H10-263086 A | 10/1998 |
| JP | H10-277156 A | 10/1998 |
| JP | H10-314308 A | 12/1998 |
| JP | H10-323391 A | 12/1998 |
| JP | H10-328303 A | 12/1998 |
| JP | H11-128349 A | 5/1999 |
| JP | H11-192304 A | 7/1999 |
| JP | H11-206885 A | 8/1999 |
| JP | P2000-152995 A | 6/2000 |
| JP | P2003-528701 A | 9/2003 |
| WO | WO-91/03207 A1 | 3/1991 |
| WO | WO-91/07201 A1 | 5/1991 |
| WO | WO-91/12845 A1 | 9/1991 |
| WO | WO-92/13587 A1 | 8/1992 |
| WO | WO-94/02191 A1 | 2/1994 |
| WO | WO-95/33506 A1 | 12/1995 |
| WO | WO-97/12640 A1 | 4/1997 |
| WO | WO-97/12641 A1 | 4/1997 |
| WO | WO-98/16273 A1 | 4/1998 |
| WO | WO-99/06093 A1 | 2/1999 |
| WO | WO-00/09189 A1 | 2/2000 |
| WO | WO-00/22985 A1 | 4/2000 |
| WO | WO-00/23135 A1 | 4/2000 |
| WO | WO-00/61212 A1 | 10/2000 |
| WO | WO-01/74431 A2 | 10/2001 |
| WO | WO-02/32490 A2 | 4/2002 |
| WO | WO-2004/030527 A1 | 4/2004 |
| WO | WO-2004/089453 A2 | 10/2004 |
| WO | WO-2005/023350 A1 | 3/2005 |
| WO | WO-2005/058394 A1 | 6/2005 |
| WO | WO-2006/026237 A1 | 3/2006 |
| WO | WO-2006/125989 A1 | 11/2006 |
| WO | WO-2008/001724 A1 | 1/2008 |
| WO | WO-2012/061869 A1 | 5/2012 |

OTHER PUBLICATIONS

Abdelatti, M.O., "A Cuff Pressure Controller for Tracheal Tubes and Laryngeal Mask Airways," Anaesthesia, 1999, 54, pp. 981-986, Blackwell Science Ltd.

Benumof, "Laryngeal Mask Airway and the ASA Difficult Airway Algorithm," Anesthesiology, 1996: 84:686-99.

Benumof, "Management of the Difficult Adult Airway with Special Emphasis on Awake Tracheal Intubation," Anesthesiology 75:1087-1110, 1991.

Bernhard et al. "Adjustment of Intracuff Pressure to Prevent Aspiration," Anesthesiology, 50: 363-366, 1979.

(56) References Cited

OTHER PUBLICATIONS

Bernhard et al., "Physical Characteristics of and Rates of Nitrous Oxide Diffusion into Tracheal Tube Cuffs," Anesthesiology 48:413-417, 1978.
Brain et al., "A New Laryngeal Mask Prototype," Anaesthesia, 1995, vol. 50, pp. 42-48.
Brain et al., "The Laryngeal Mask Airway, Development and Preliminary Trials of a New Type of Airway," Anaesthesia, 1985, vol. 40, pp. 356-361.
Brain, "The Laryngeal Mask—A New Concept in Airway Management," Br. J. Anaesth. (1983), 55, 801-805.
Brain, "The Laryngeal Mask Airway—A Possible New Solution to Airway Problems in the Emergency Situation," Archives of Emergency Medicine, 1984, 1, 229-232.
Brain, "Three Cases of Difficult Intubation Overcome by the Laryngeal Mask Airway," Anaesthesia, 1985, vol. 40, pp. 353-355.
Brimacombe, "The Split Laryngeal Mask Airway," Anaesthesia, Jul. 1993;48(7):639.
Brodrick et al, "The Laryngeal Mask Airway, A Study of 100 Patients During Spontaneous Breathing," Anaesthesia, 1989, vol. 44, pp. 238-241.
Burgard et al, "The Effect of Laryngeal Mask Cuff Pressure on Postoperative Sore Throat Incidence," Journal of Clinical Anesthesia 8:198-201, 1996.
Caplan et al, "Adverse Respiratory Events in Anesthesia: A Closed Claims Analysis," Anesthesiology 72:828-833, 1990.
Craven, "Prevention of Hospital-Acquired Pneumonia: Measuring Effect in Ounces, Pounds, and Tons," Annals of Internal Medicine, vol. 122, No. 2, pp. 229-231 (Feb. 1, 1995).
Cuff-Pressure Control CDR 2000, Technical Data, 4 pages, Manufacturer ESW-EXTEL Systems Wedel, Gesellschaft fur Ausrustung mbH, 2000.
Davies et al, "Laryngeal Mask Airway and Tracheal Tube Insertion by Unskilled Personnel," The Lancet, 1990; 336:977-79.
de Mello et al, "The Use of the Laryngeal Mask Airway in Primary Anaesthesia," Anaesthesia. Sep. 1990;45(9):793-4.
Doyle et al, "Intraoperative Awareness: A Continuing Clinical Problem," Educational Synopses in Anesthesiology and Critical care Medicine, The Online Journal of Anesthesiology vol. 3 No. 6, 8 pages, Jun. 1996.
Engbers "Practical Use of Diprifusor" Systems, Anaesthesia, 1998, 53, Supplement 1, pp. 28-34.
Eriksson et al, "Functional Assessment of the Pharynx at Rest and During Swallowing in Partially Paralyzed Humans," Anesthesiology vol. 87, No. 5, pp. 1035-1042, Nov. 1997.
Glen, "The Development of 'Diprifusor': a TCI System for Propofol," Anaesthesia, 1998, 53, Supplement 1, pp. 13-21.
Gray et al, "Development of the Technology for 'Diprifusor' TCI Systems," Anaesthesia, 1998, Supplement 1, pp. 22-27.
Heath, "Endotracheal Intubation Through the Laryngeal Mask—Helpful When Laryngoscopy is Difficult or Dangerous," European Journal of Anaesthesiology, 1991, Supplement 4, 41-45.
Hickey et al, "Cardiovascular Response to Insertion of Brain's Laryngeal Mask," Anaesthesia, 1990, vol. 45, pp. 629-633.
Inomata et al, "Transient Bilateral Vocal Cord Paralysis After Insertion of a Laryngeal Mask Airway," Anaesthesiology,82;787-788, 1995.
International Search Report in PCT/GB2006/001913 dated Aug. 26, 2006.
Jacobson et al, "A Study of Intracuff Pressure Measurements, Trends and Behaviour in Patients During Prolonged Periods of Tracheal Intubation," Br. J. Anaesth. (1981), 53, 97-101.
Kambic et al, "Intubation Lesions of the Larynx," Br. J. Anaesth. (1978), 50, 587-590.
Kangas, "Neurometric Assessment of Adequacy of Intraoperative Anesthetic," Pacific Northwest National Laboratory, retrieved May 13, 2008, 3 pages.
Kapila, et al., "Proceedings of the Anaesthetic Research Society, Leeds Meeting, Mar. 31-Apr. 1, 1995," British Journal of Anaesthesia, 1995, 75:228P-229P.
Lindholm, "Methods," ACTA Anaesthesiologica Scandinavica, Prolonged Endotracheal Intubation, Chapter III, pp. 32-46 (1969).
Majumder et al, "Bilateral Lingual Nerve Injury Following the Use of the Laryngeal Mask Airway," Anaesthesia, 1998, 53, 169-191.
Martin, Patentability of Methods of Medical Treatment: A Comparative Study, J. Pat & Trademark Off. Soc'y, pp. 381-423, 2000.
Miller, "A Pressure Regulator for the Cuff of the Tracheal Tube," Anaesthesia, 1992, vol. 47, pp. 594-596.
Muthuswamy et al., "The Use of Fuzzy Integrals and Bispectral Analysis of the Electroencephalogram to Predict Movement Under Anestheia," Transactions on Biomedical Engineering, vol. 46, No. 3, Mar. 1999.
Nagai et al., "Unilateral hypoglossal nerve paralysis following use of the laryngeal mask airway," Anaesthesia, vol. 49, pp. 603-406, 1994.
Observations by a third party concerning European Patent Application No. 99 947 765.6 dated Jan. 18, 2005, 4 pages.
Patel et al., "Tracheal Tube Cuff Pressure," Anaesthesia, vol. 39, pp. 862-864, 1984, 3 pages.
Pennant et al., "Comparison of the Endotracheal Tube and Laryngeal Mask in Airway Management by Paramedical Personnel," Anesth. Analog, pp. 531-534, 1992.
Pippin et al., "Long-term tracheal intubation practice in the United Kingdom," Anaesthesia, vol. 38, pp. 791-795, 1983.
Raeder et al., "Tracheal tube cuff pressures," Anaesthesia, vol. 40, pp. 444-447, 1985.
Response to Complaint in *LMA Deutschland Gmbh* v. *AMBU (Deutschland) Gmbh*, dated Feb. 10, 2006.
Rieger et al., "Intracuff Pressures Do Not Predict Laryngopharyngeal Discomfort after Use of the Laryngeal Mask Airway," Anesthesiology, vol. 87, No. 1, Jul. 1997, pp. 63-67.
Seegobin et al., "Endotracheal cuff pressure and tracheal mucosal blood flow: endoscopic study of effects of four volume cuffs," British Medical Journal, vol. 288, Mar. 1984, pp. 965-968.
Willis, et al., "Tracheal tube cuff pressure," Anaesthesia, vol. 43, pp. 312-314, 1988.
Worthington, et al., "Proceedings of the Anaesthetic Research Society, Leeds Meeting, Mar. 31-Apr. 1, 1995," British Journal of Anaesthesia, 1995, 75:228P.
Wynn et al., "Tongue Cyanosis after Laryngeal Mask Airway Insertion," Anesthesiology, vol. 80, No. 6, Jun. 1994.
Merriam Webster's Collegiate Dictionary, 10$^{th}$ Ed., 1997, pp. 254 and 1029, definitions of Convex and Saddle.
Neurometric Assessment of Adequacy of Intraoperative Anesthetic. Mar. 1999, 3 pages, www.pnl.gov/medical/info/neuro.htm.
Office Action issued on Sep. 15, 2014 in U.S. Appl. No. 13/254,594 (US 2012/0048279).
Office Action issued on May 20, 2015 in U.S. Appl. No. 13/254,594 (US 2012/0048279).
Office Action issued on Sep. 15, 2015 in U.S. Appl. No. 13/254,594 (US 2012/0048279).
Office Action issued on Jan. 13, 2016 in U.S. Appl. No. 13/254,594 (US 2012/0048279).
Office Action issued on Mar. 28, 2013 in U.S. Appl. No. 13/397,488 (U.S. Pat. No. 8,716,871).
Office Action issued on Jul. 19, 2013 in U.S. Appl. No. 13/397,488 (U.S. Pat. No. 8,716,871).
Notice of Allowance issued on Dec. 16, 2013 in U.S. Appl. No. 13/397,488 (U.S. Pat. No. 8,716,871).
Office Action issued on Oct. 17, 2012 in U.S. Appl. No. 12/518,776 (US 2010/0089393).
Office Action issued on Apr. 24, 2013 in U.S. Appl. No. 12/518,776 (US 2010/0089393).
Office Action issued on Mar. 17, 2014 in U.S. Appl. No. 12/518,776 (US 2010/0089393).
Office Action issued on Jul. 2, 2014 in U.S. Appl. No. 12/518,776 (US 2010/0089393).
Office Action issued on Nov. 26, 2014 in U.S. Appl. No. 12/518,776 (US 2010/0089393).
Office Action issued on Apr. 15, 2015 in U.S. Appl. No. 12/518,776 (US 2010/0089393).
Office Action issued on Oct. 2, 2015 in U.S. Appl. No. 12/518,776 (US 2010/0089393).

(56) References Cited

OTHER PUBLICATIONS

Office Action issued on May 25, 2012 in U.S. Appl. No. 11/915,558 (US 2010/0059061).
Office Action issued on Feb. 14, 2013 in U.S. Appl. No. 11/915,558 (US 2010/0059061).
Office Action issued on May 24, 2013 in U.S. Appl. No. 11/915,558 (US 2010/0059061).
Office Action issued on Oct. 23, 2013 in U.S. Appl. No. 11/915,558 (US 2010/0059061).
Office Action issued on Jul. 14, 2014 in U.S. Appl. No. 11/915,558 (US 2010/0059061).
Office Action issued on Dec. 16, 2014 in U.S. Appl. No. 11/915,558 (US 2010/0059061).
Office Action issued on Apr. 8, 2015 in U.S. Appl. No. 11/915,558 (US 2010/0059061).
Office Action issued on Jan. 13, 2016 in U.S. Appl. No. 11/915,558 (US 2010/0059061).
Office Action issued on May 13, 2015 in U.S. Appl. No. 14/029,831 (US 2014/0087380).
Office Action issued on Jul. 22, 2015 in U.S. Appl. No. 11/915,558 (US 2010/0059061).
Notice of Allowance issued on Dec. 11, 2012 in U.S. Appl. No. 11/915,558 (US 2010/0059061).
Office Action issued on Oct. 16, 2015 in U.S. Appl. No. 13/981,829 (US 2014/0034060).
Brimacombe, "Laryngeal Mask Anesthesia—Principles and Practice," $2^{rd}$ edition, Chapters 1-22, Appendices A-C, Saunders/Elsevier Limited, 2005.
Benumof, "The Glottic Apeture Seal Airway," Anesthesiology, vol. 88, No. 5, pp. 1219-1226, May 1998.
Brimacombe, "Anatomy," Laryngeal Mask Anesthesia—Principles and Practice, Chapter 3, pp. 73-101, 2005.
Ishimura et al, "Impossible Insertion of the Laryngeal Mask Airway and Oropharyngeal Axes," Anesthesiology, vol. 83, No. 4, pp. 867-869, Oct. 1995.
McIntyre, "History of Anaesthesia—Oropharyngeal and nasopharyngeal airways: I (1880-1995)," Canadian Journal of Anaesthesia, vol. 43, No. 6, pp. 629-635, 1996.
Miller, "A Proposed Classification and Scoring System for Supraglottic Sealing Airways: A Brief Review," Anesth. Analg., vol. 99, pp. 1553-1559, 2004.
Verghese et al., "Clincial assessment of the single use laryngeal mask airway—the LMA-Unique", British Journal of Anaesthesia, vol. 80, pp. 677-679, 1998.
International Organization for Standardization, "Anaesthetic and respiratory equipment—Supralaryngeal airways and connectors," ISO 11712, First edition, pp. 1-27, May 15, 2009.
Office Action issued on Mar. 22, 2016 in U.S. Appl. No. 13/981,829 (US 2014/0034060).

\* cited by examiner

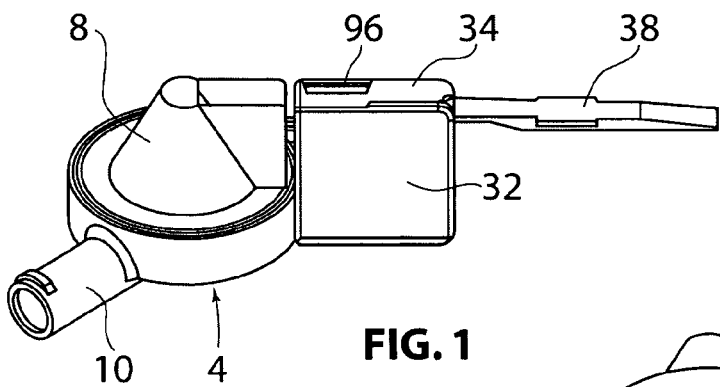
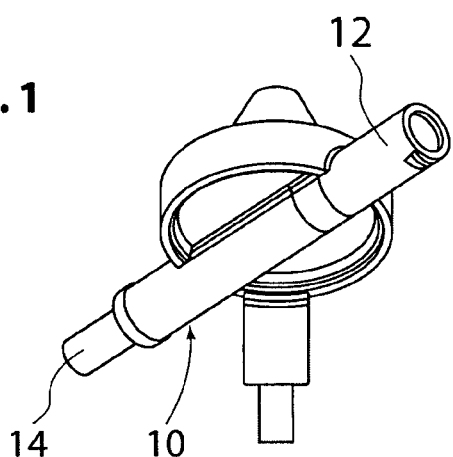
FIG. 1
FIG. 2
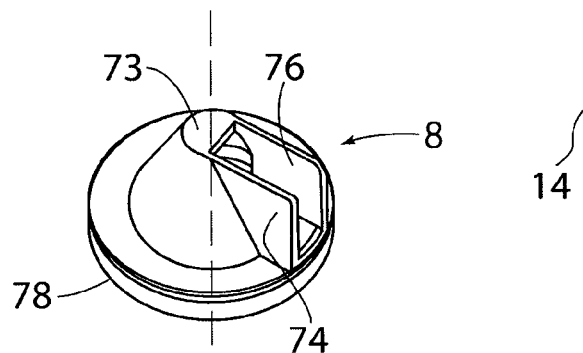
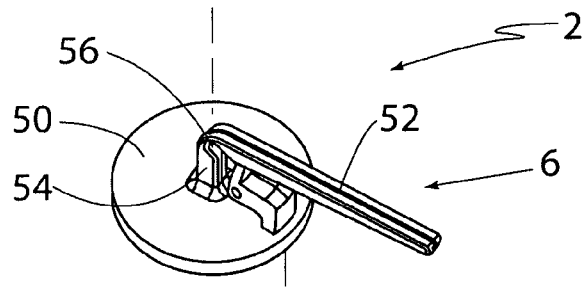
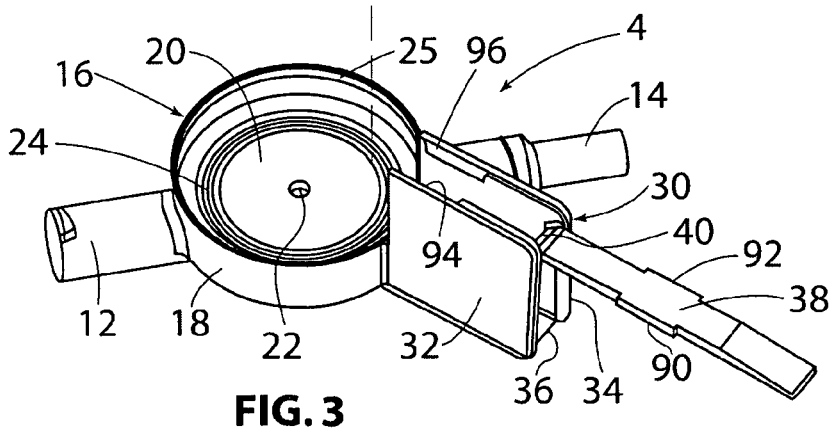
FIG. 3

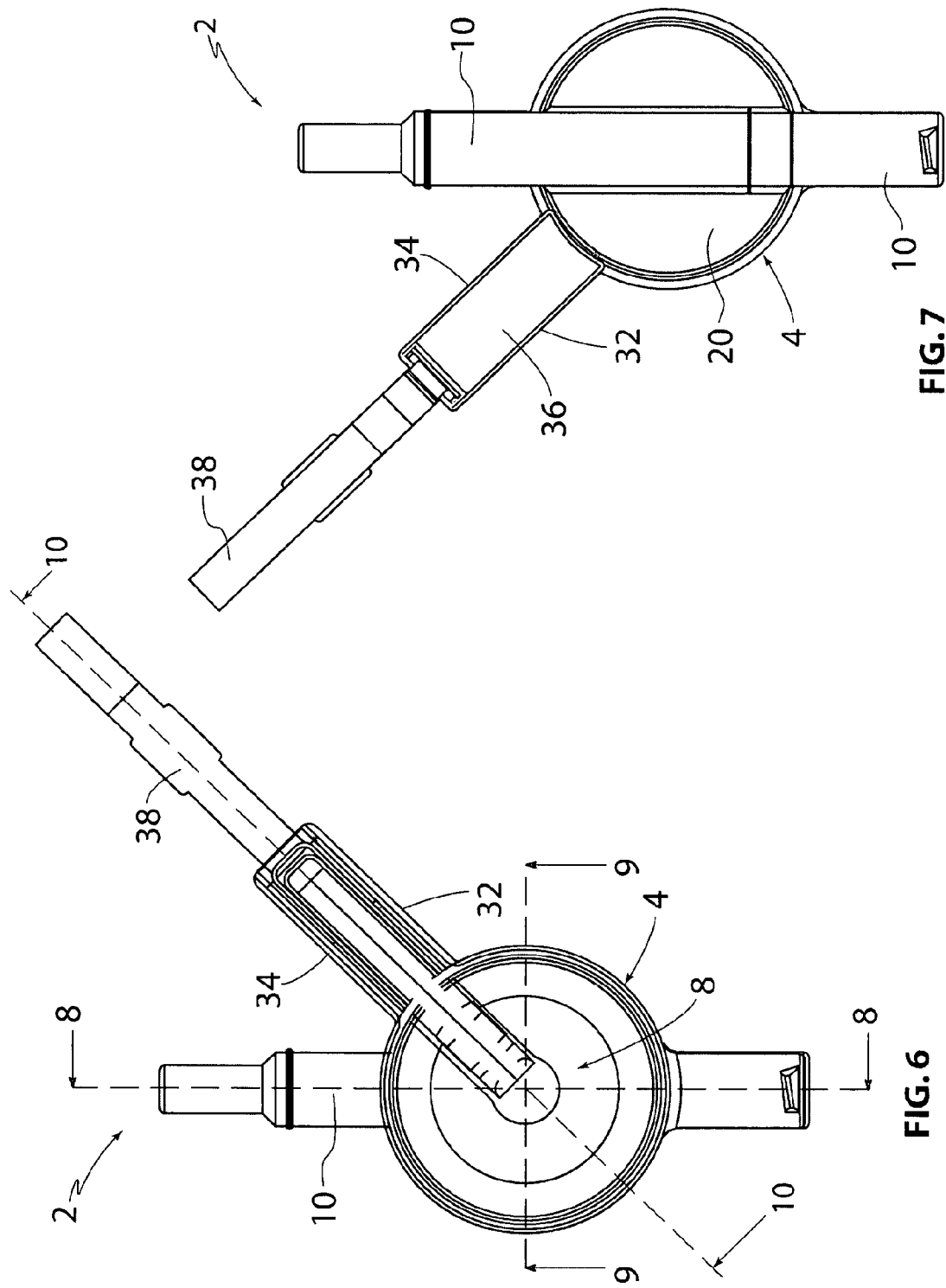

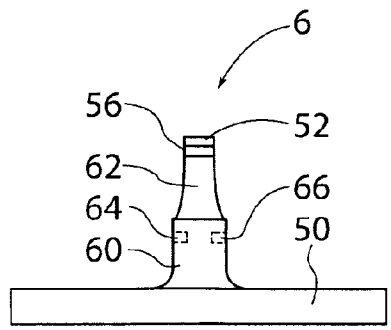
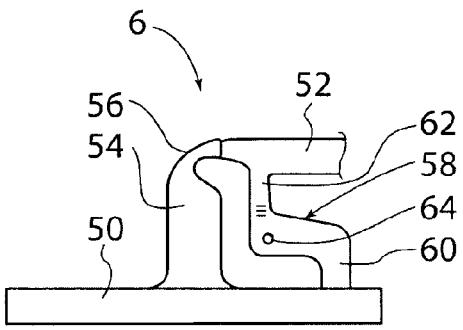
FIG. 14        FIG. 15
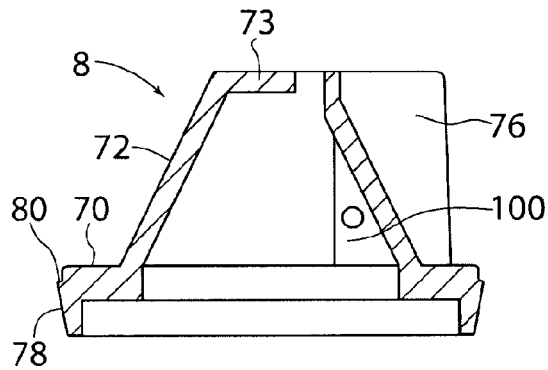
FIG. 16
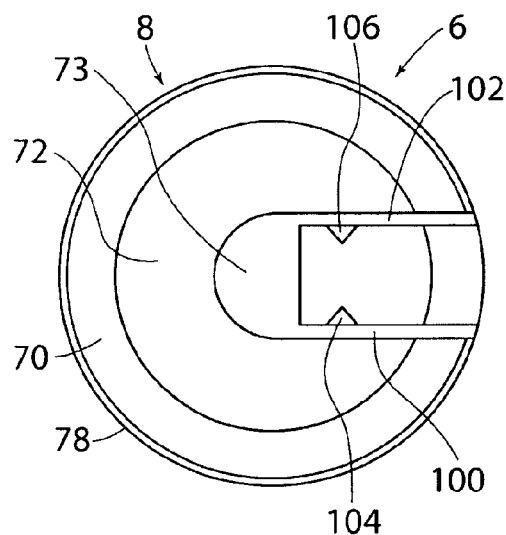
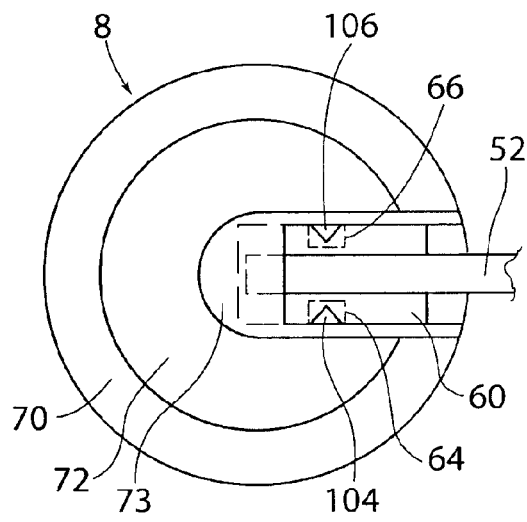
FIG. 17        FIG. 18

PRESSURE INDICATOR

This invention relates to a pressure indicator.

There are many applications where a low cost pressure indicator is required for indicating the pressure of a liquid or gas. Sometimes the liquid or gas is flowing and at other times it is hydrostatic.

In the medical field, contamination is also a serious problem and it would be highly desirable for pressure indicators to be available which were inexpensive so that they could be discarded after a single use.

Medical applications include monitoring of the pressure of injectable fluids in typical situations as follows:

(i) Injections

During the injection of therapeutic agents into human tissue high pressures should be avoided where this indicates that the site of the injection is other than intended. Arterial injection produces pulsatile pressures of >100 mmHg. Injection into nerves characteristically produce static pressures of >1000 mmHg. Injection into tendon's and other non porous tissues may produce even higher pressures. There is often a need for the physician or nurse to be aware of such pressures as the tactile force applied to a syringe is not a consistent guide to the pressures generated due to variation in piston diameter between syringes of differing capacity.

(ii) Flow Rate Monitoring

If a fluid is injected through a fixed resistance then the pressure provides an indication of flow rate which is desirable during the injection of antibiotics, chemotherapeutic agents and radiological dyes. Such a pressure gauge can be calibrated to show the desired flow rate and hence the physician or nurse can easily inject the agent within the manufacturer's guidelines.

(iii) Pressure Monitoring for Ancillary Equipment

Many medical devices require pressure monitoring as part of their functionality. The pneumatic pressure devices commonly used to force fluid from Intravenous fluid bags require a pressure gauge for correct pressurisation. Filling of various catheters placed in body cavities arteries etc. These have balloons that are inflated to provide mechanical force to seal or expand against the walls for such cavities or vessels.

(iv) Measurement of Airway Pressure

Various airway management devices (including resuscitation bags) provide positive pressure ventilation for patients lungs, monitoring of this pressure is desirable to avoid barotrauma to the lungs.

The characteristics that are important for such a device include:

(i) Cost

Low cost requires low cost components and as well as ease of manufacture.

(ii) Ease of Use

Pressure indication that is easily read and preferably with an analogue indicating scale for easy interpretation.

(iii) Minimal Dead Space

If the gauge is used for the injection of fluids it is important that the internal mechanism of the gauge has minimal dead space as this tends to introduce air into the injection system. Further, the therapeutic agent may be of great value and hence it is undesirable for it to fill the gauge's deadspace and hence to unavailable for injection. Finally the presence of air in the gauge can blunt the response of the gauge to pressure change.

(iv) Compact Design

It is important that the gauge be of the minimum size practical as in many applications it is undesirable to have a bulky or heavy device attached to a syringe or other system.

(v) Accuracy

It is important for such a gauge to have appropriate level of accuracy. +/−7.5% has been achieved.

It is a general object of the invention to provide a pressure indicator which at least partially satisfies all or some of the criteria above.

According to the present invention there is provided a pressure indicator:

a body having a pressure chamber which has an inlet for communication with a fluid;

a resilient diaphragm having a periphery sealed against the body and having one side thereof exposed to the fluid within the chamber;

an indicating arm having an inner end which is integrally formed with the other side of the diaphragm and an outer end arm which is adjacent to a scale, the arrangement being such that pressure of the fluid within the chamber causes resilient deformation of the diaphragm which in turn causes the outer end of the arm to move relative to the scale thereby indicating the pressure of the fluid in the chamber.

Preferably, the chamber has an outlet and said fluid under pressure, in use, flows from the inlet to the outlet through the chamber.

Preferably, the indicator includes a fulcrum which serves to cause rotation of the arm on resilient deformation of the diaphragm.

Preferably, the fulcrum is integrally formed with the diaphragm.

Preferably, the diaphragm, arm and fulcrum are injection moulded from plastics material.

Preferably, the indicator includes a first housing coupled to the body, the diaphragm being arranged to resiliently expand into the first housing when the pressure of the fluid increases.

Preferably, the first housing includes formations which interlock with complementary formations on the body and wherein, in use, the periphery of the diaphragm is clamped between the body and the first housing.

Preferably, the fulcrum extends from a mounting point inwardly adjacent to the periphery of the diaphragm.

Preferably, the first housing includes guide means which engage or are engagable with the fulcrum to limit displacement of the fulcrum when the diaphragm expands.

Preferably, the indicator includes a second housing, the outer end of the indicating arm being located within the second housing.

Preferably, the second housing is integrally formed with the body.

The invention also provides a resilient diaphragm for use in a pressure indicator having a periphery which is, in use, exposed to the fluid within a chamber, and an indicating arm having an inner end which is integrally formed with the diaphragm and an outer end arm which is adjacent, in use, to a scale.

The invention also provides a pressure indicator:

a body having a pressure chamber which has an inlet for communication with a fluid under pressure;

a resilient diaphragm having a periphery sealed against the body and having one side thereof exposed to the fluid within the chamber;

an indicating arm having an inner end which is integrally formed with the other side of the diaphragm and an outer end arm which is adjacent to a scale;

a first housing includes formations which interlock with complementary formations on the body and wherein, in use, the periphery of the diaphragm is clamped between the body and the first housing, the arrangement being such that pressure within the chamber causes resilient deformation of the diaphragm which in turn causes the outer end of the arm to move relative to the scale thereby indicating the pressure of the fluid in the chamber, characterised in that the indicator is formed from only three components.

The invention also provides a pressure indicator:

a body having a pressure chamber which has an inlet for communication with fluid under positive or negative pressure relative to atmosphere;

a resilient diaphragm having a periphery sealed against the body and having one side thereof exposed to the fluid within the chamber;

an indicating arm having an inner end which is integrally formed with the other side of the diaphragm and an outer end arm which is adjacent to a scale, the arrangement being such that pressure within the chamber causes resilient deformation of the diaphragm which in turn causes the outer end of the arm to move relative to the scale thereby indicating the pressure of the fluid in the chamber.

The invention will now be further described with reference to the accompanying drawings, in which:

FIG. 1 is an isometric view of a pressure indicator of the invention;

FIG. 2 is an underside isometric view of the indicator;

FIG. 3 is an exploded view of the indicator;

FIG. 6 is a plan view of the indicator;

FIG. 7 is an underside view of the indicator;

FIG. 14 is a side view of the diaphragm;

FIG. 15 is another side view of the diaphragm;

FIG. 16 is a fragmentary view of part of the housing;

FIG. 17 is a fragmentary underside view of the housing;

FIG. 18 is a schematic plan view of the housing and part of the diaphragm;

Figure 4:
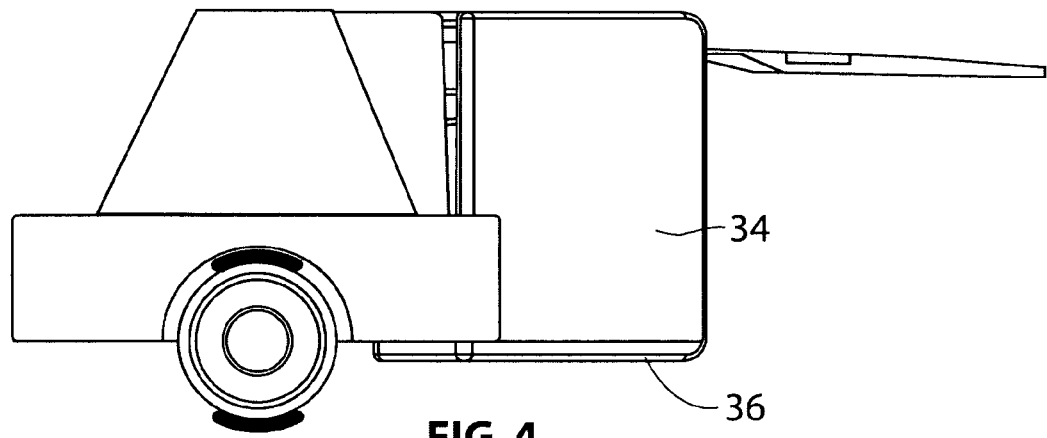
FIG. 4 is a side view of the indicator.
Figure 5:
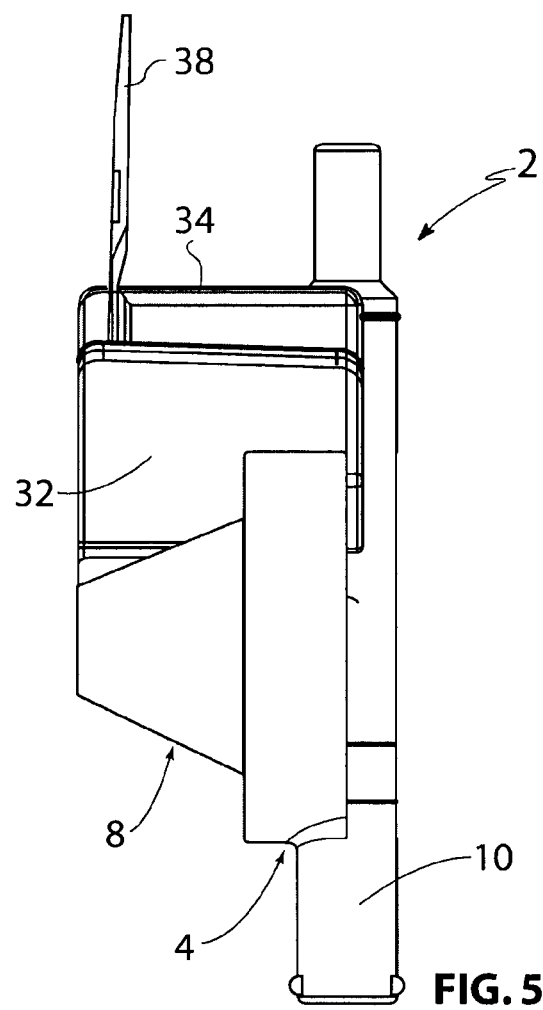
FIG. 5 is another side view of the indicator.
Figure 9:
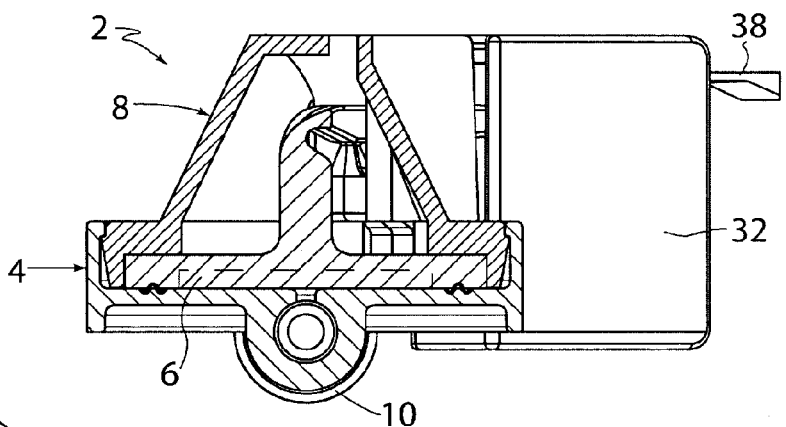
FIG. 9 is a cross-sectional view along the line 9-9.

The drawings show a pressure indicating device 2 of the invention which is especially suited for single use medical applications such as indicating the pressure at which a liquid is injected into a patient via a syringe. Typically the pressure of the fluid needs to be in the range from 0 to 25 psi.

The indicating device 2 of the invention is made from three components which include a main body 4 (also referred to as a "body"), diaphragm assembly 6 and diaphragm housing 8 as best seen in the exploded view of FIG. 3.

The main body 4 is preferably injection moulded from plastics material such as clear polycarbonate. The main body 4 includes a conduit 10 which has an inlet 12 formed as a male Luer connector and an outlet 14 formed as a female Luer connector. The inlet and outlets could be interchanged. The conduit 10 is integrally formed with a cup-shaped body 16 which includes a cylindrical wall 18 and base wall 20. The base wall 20 includes a port 22 which communicates with the interior of the conduit 10. The base wall 20 is essentially flat or planar but it does include an annular projecting rib 24 located somewhat inwardly from the cylindrical wall 18. The cylindrical wall 18 includes an inwardly projecting lip 25 on its upper edge.

Figure 8:
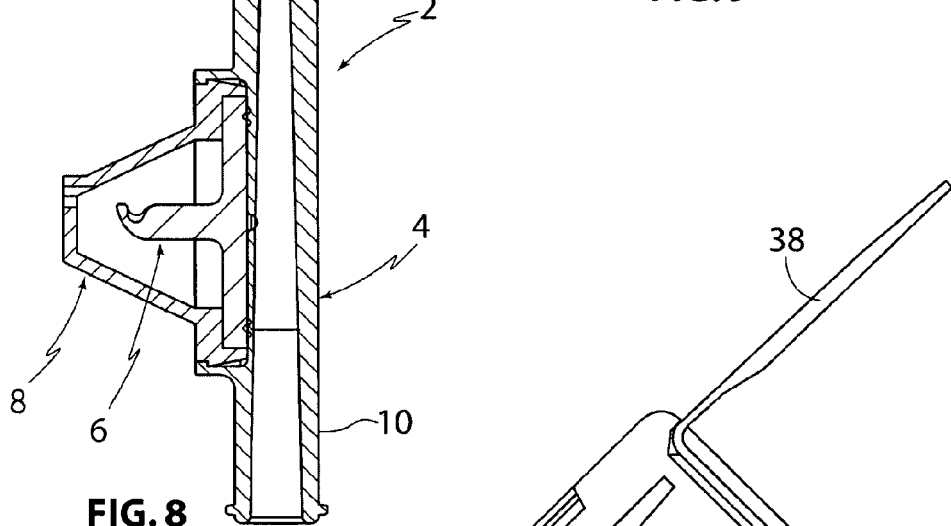
FIG. 8 is a cross-sectional view along the line 8-8.
Figure 10:
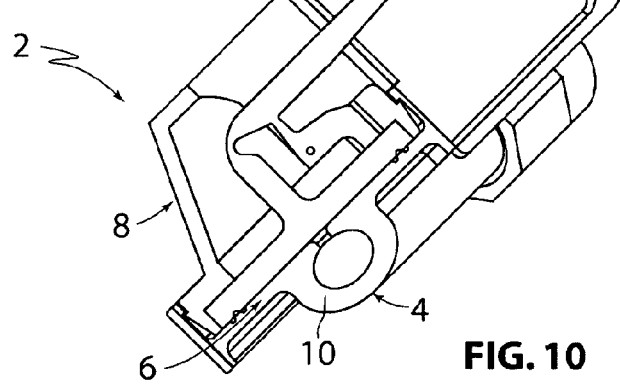
FIG. 10 is a cross-sectional view along the line 10-10.
Figure 11:
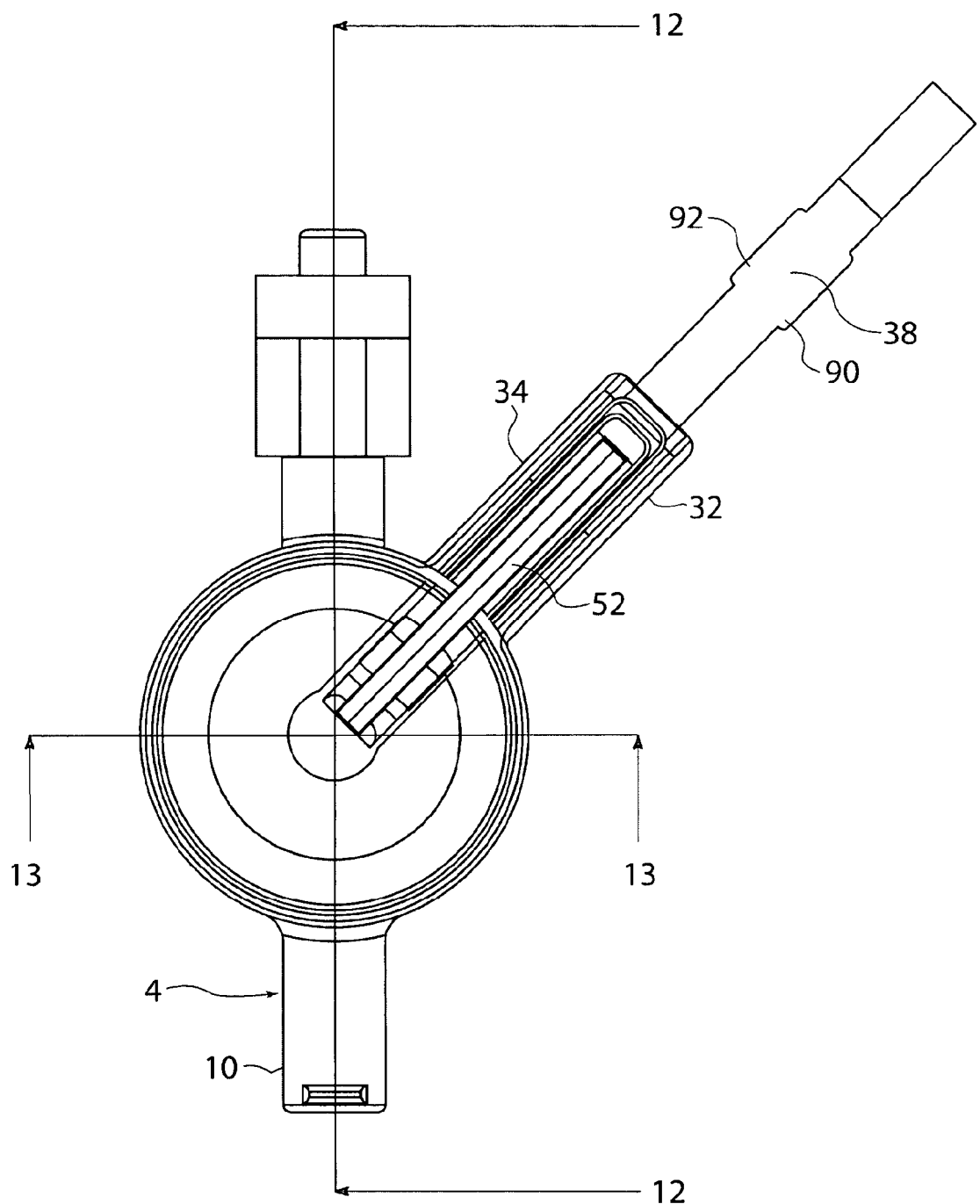
FIG. 11 is an enlarged plan view.
Figure 12:
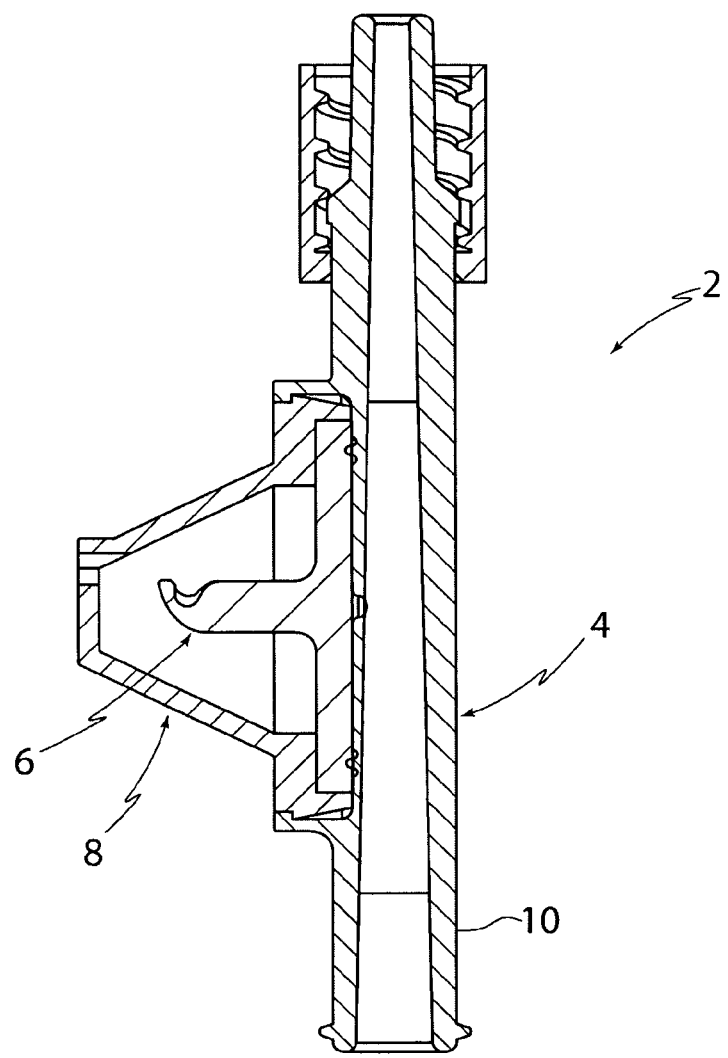
FIG. 12 is a cross-sectional view along the line 12-12.

The main body 4 is integrally formed with an indicator housing 30 which is formed at an angle of about 45° relative to the axis of the conduit 10 as seen in FIG. 8. This orientation makes it easier to view the pressure indication as will be described in more detail below. The indicator housing 30 includes two parallel sidewalls 32 and 34 joined by a bottom wall 36. The housing includes a top wall 38 which is moulded in a position where it is generally parallel to the bottom wall 36 and connected to the upper corners of the sidewalls 32 and 34 by means of an integral hinge 40. This is the preferred way of forming the top wall because it would be difficult to injection mould the main body 4 with a fixed top wall joining the upper edges of the sidewalls 32 and 34. One or other of the walls 32 or 34 could be moulded with a pressure scale (not shown) which in use is adjacent to the indicating arm of the device so as to enable the pressure to be read. Alternatively, the scale could be printed onto one or other of these walls. Normally it is preferred that the scale be printed onto the sidewall 34 so that an operator can view the position of the indicating arm through the sidewall 32 against the scale so as to obtain a pressure reading.

The diaphragm assembly 6 will now be described in more detail with reference to FIGS. 3, 14 and 15. The diaphragm assembly is injection moulded from silicone rubber preferably having a Shore A hardness in the range 50 to 55. It includes a diaphragm 50 in the form of a circular disc preferably of uniform thickness, the thickness typically being in the range from 1.5 mm to 2.5 mm and preferably about 2 mm. The diaphragm is integrally moulded with an indicating arm 52 which is joined to the centre of the diaphragm 50 by means of an upstanding post 54 via an integral hinge 56. The diaphragm assembly 6 includes a bracket 58 which is also integrally moulded with the diaphragm 50 and the indicating arm 52. The bracket 58 includes a lower leg which is connected to the diaphragm 50 at a mounting point inwardly adjacent to the periphery of the diaphragm, as best seen in FIG. 15. The bracket includes a second leg 62 which is joined to the underside of the indicating arm 52 and serves as a fulcrum about which the indicating arm 52 can rotate, as will be described in more detail below. As can be seen from FIG. 14, the first leg 60 is somewhat wider than the second leg 62. Also, the first leg 60 includes first and second blind bores 64 and 66.

The diaphragm housing 8 will now be described in more detail with reference to FIGS. 3, 13, 16, 17 and 18.

Figure 13:
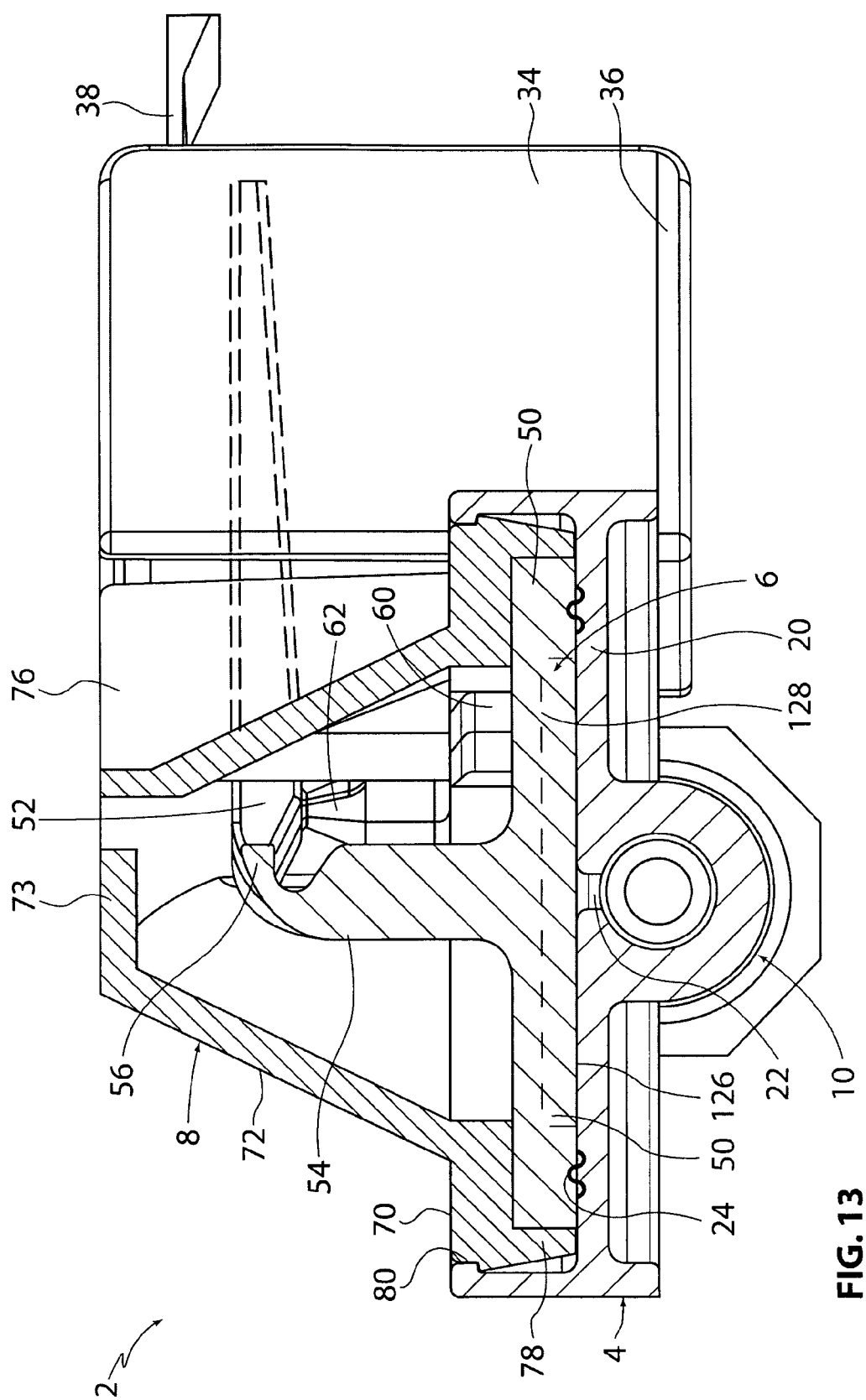
FIG. 13 is an enlarged side view.

The diaphragm housing 8 is injection moulded from clear polycarbonate as an integral moulding. It includes an annular base 70 from which extends a hollow frustoconical projection 72 which is partly closed by means of a top wall 73. As can best be seen from FIG. 3, the frustoconical projection 72 includes a gap which is bounded by two flanges 74 and 76 which extend from the annular base 70 to the top wall 73. The housing 8 includes a tapered flange 78 which extends downwardly from the outer periphery of the base 70, as best seen in FIG. 13. In addition, the outer peripheral edge of the annular base 70 includes a rebate 80.

The arrangement and dimensions of the three components are such that the diaphragm 50 is clamped between the main body 4 and the housing 8 with the indicating arm 52 projecting between the flanges 74 and into the indicator housing 30. More particularly, it will be seen from FIG. 13 that the diaphragm 50 rests on the base wall 20 of the main body 4. Its outer peripheral region engages the underside of the annular base 70 of the housing 8 and the outer peripheral wall engages the inner periphery of the flange 78. During assembly, the diaphragm assembly is first fitted into the diaphragm housing 8 so that the indicating arm 52 projects outwardly between the flanges 74 and 76. The indicating arm 52 is aligned relative to the sidewalls 32 and 34 so that the diaphragm housing 8 and diaphragm assembly 6 can be lowered so that the indicating arm 52 enters the indicator housing 30 between the sidewalls 32 and 34. The diaphragm housing 8 and main body 4 are then pressed together so that the tapered flange is snap fit into the cylindrical 18 and the lip 25 interlocks with the rebate 80 so that the diaphragm housing 8 and main body 4 are interlocked with the diaphragm 50 sealingly engaged therebetween. It will be seen from FIG. 13 that the rib 24 presses into the underside of the diaphragm 50 and resiliently deforms it so as to enhance the seal between the outer region of the diaphragm 50 and the base wall 20 of the main body 4.

Figure 19:
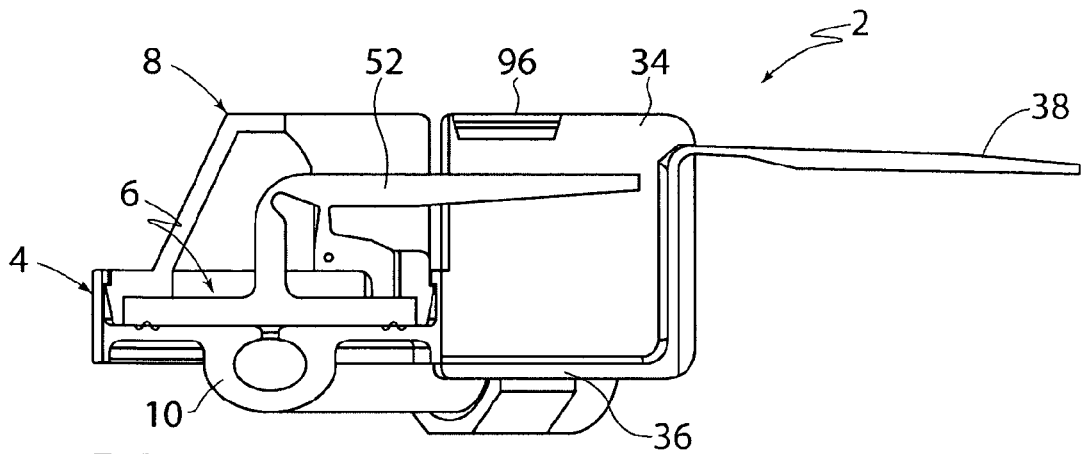
FIG. 19 is a side view of the indicator.
Figure 20:
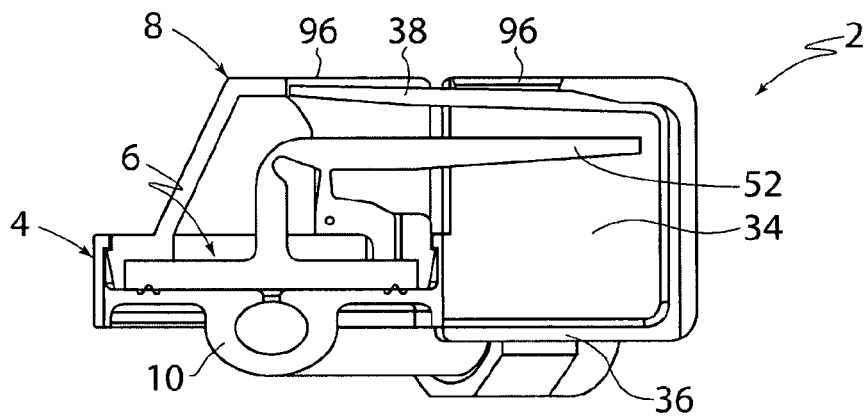
FIG. 20 shows the indicator in its final assembled position.
Figure 21:
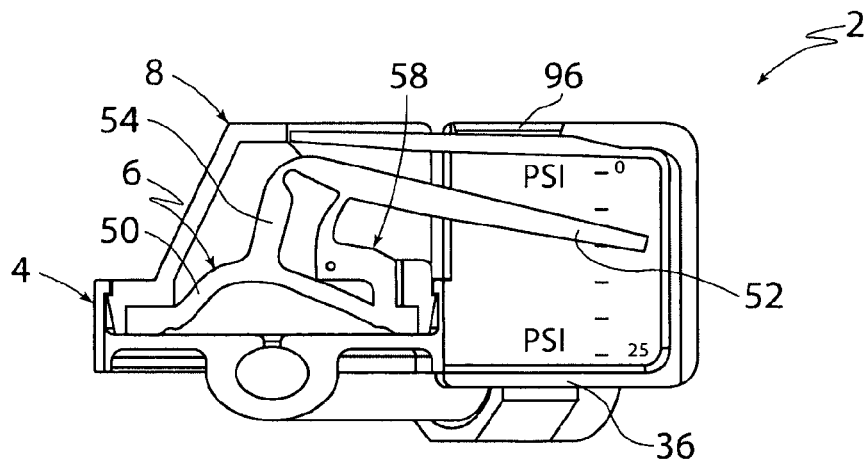
FIG. 21 shows the indicator with the diaphragm deflected.

After the three components have been fitted together, as described above, the top wall 38 can be rotated into its final position. This is schematically illustrated in FIGS. 19 and 20 where the top wall has been rotated anti-clockwise through approximately 180° so that the top wall 38 closes the gap between the sidewalls 32 and 34 and is sufficiently long so that it effectively closes the gap between the flanges 74 and 76. This protects the indicating arm 52 from being inadvertently displaced. The top wall 38 includes laterally extending projections 90 and 92 which interlock with complementary projections 94 and 96 formed adjacent to the upper edges of the sidewalls 32 and 34.

In use of the pressure indicating device 2 of the invention, fluid under pressure is located within the conduit 10. The fluid can be static or flowing. The port 22 communicates the pressurised fluid with the underside of the diaphragm 50 and, depending on the pressure of the fluid, the diaphragm 50 will resiliently deform, as schematically illustrated in FIG. 20. It will be appreciated that as the diaphragm 50 deflects upwardly, the indicating arm 52 will be caused to rotate in a generally clockwise direction as seen in FIG. 20. The extent of deflection of the indicating arm 52 is proportional to the extent of deflection of the diaphragm 50. Deflection of the diaphragm 50 is also generally proportional to the pressure within the conduit 10, as will be described in more detail below.

It will be appreciated that the second leg 62 which serves as the fulcrum for the indicating arm 52 is not completely independent of movement of the diaphragm 50 since it forms part of the bracket 58 which is moulded integrally with the diaphragm 50. The illustrated device includes components which serve to stabilise the position of the indicating arm 52 so as to tend to make deflection of the indicating arm 52 more truly proportional to the pressure within the conduit 10. In the illustrated arrangement, the width of the first leg 60 is such that it is snugly received between inner flanges 100 and 102 which can be regarded as being contiguous with the flanges 74 and 76 respectively. The flanges 100 and 102 have inwardly directed conical pins 104 and 106 formed therewith. The arrangement is such that the conical pins 104 and 106 are received within the bores 64 and 66 respectively as shown in the schematic plan view of FIG. 18. This serves to further fix the position of the legs 60 and 62 relative to the main body 4 and diaphragm housing 8 so as to minimise movement of the fulcrum for the indicating arm 52.

A prototype of the pressure indicating device 2 has been constructed and tested. In the prototype, the diaphragm 50 had a nominal diameter of 18 mm and the length of the indicating arm 52 about 22 mm as measured from the centre line of the post 54.

The deflection of the diaphragm depends on the thickness of the diaphragm as well as its hardness. Table 1 below shows the typical deflection at the end of the indicating arm 52 for diaphragms of different thicknesses. In each case the hardness was Shore A 50.

| Diaphragm Thickness (mm) | Deflection of indicator at 25 psi (mm) |
| --- | --- |
| 1.6 | 12.8 |
| 1.8 | 8.4 |
| 2.0 | 5.8 |

Figure 22:
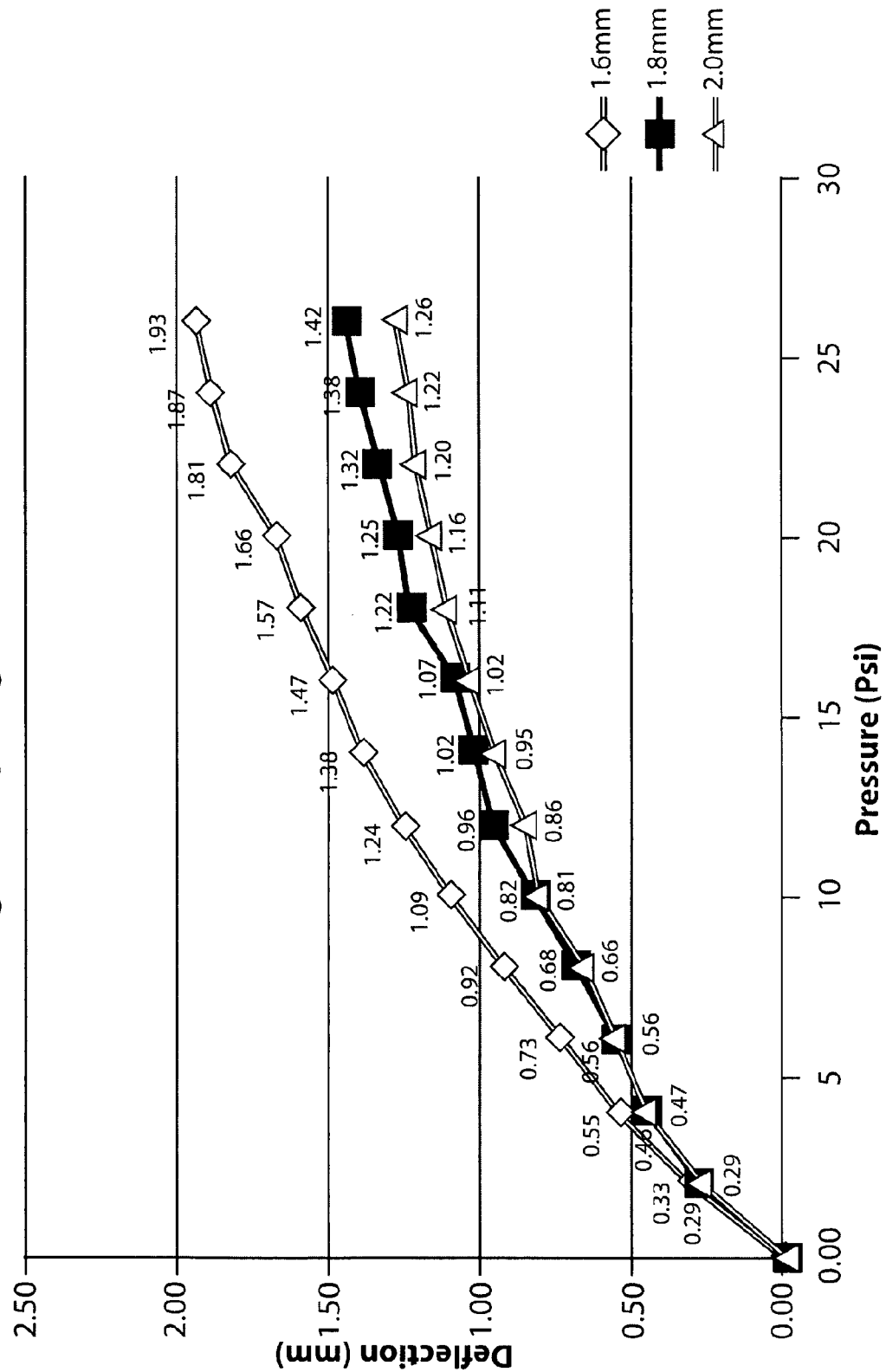
FIG. 22 is a graph showing the deflection of the diaphragm as a function of pressure.
Figure 23:
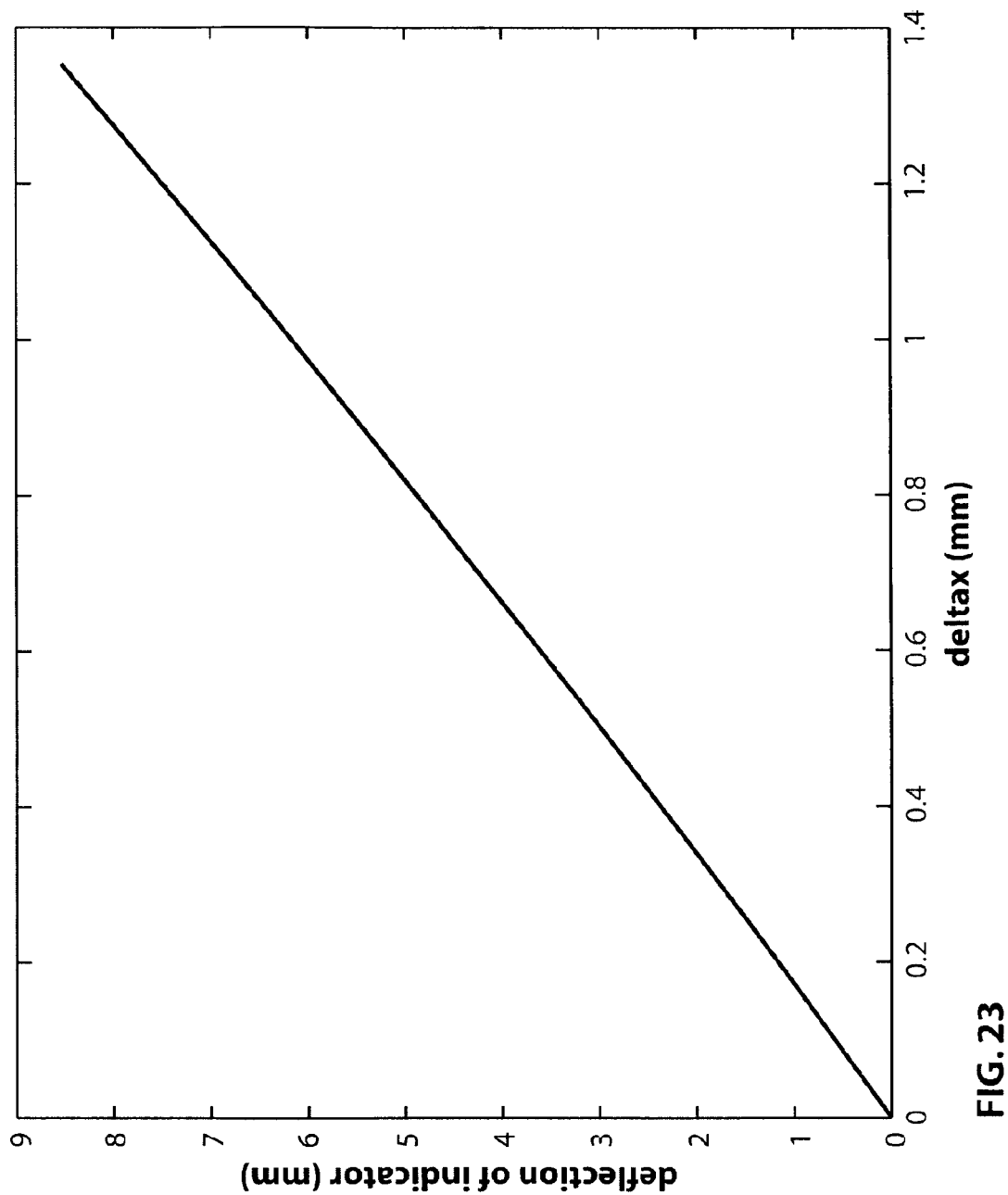
FIG. 23 is a diagram showing deflection of the indicator as a function of deflection of the diaphragm.

FIG. 22 shows the average deflection of the diaphragm 50 as a function of the pressure within the conduit 10. FIG. 23 is a diagram showing the theoretical deflection at the tip of the indicating arm 52 as a function of deflection of the diaphragm. It will be seen that the relationship is approximately linear.

In the illustrated arrangement, the main body 4 is formed with a conduit 10 which has an inlet and outlet which is appropriate for pressure measurement where the fluid under pressure flows through the conduit. It would be possible to block one of the outlets where the device was to be used for measurement of a fluid which is not flowing through the device. Alternatively, the main body 4 could be moulded with a single inlet port without an outlet.

The pressure indicator 2 described above is a compact and inexpensive device for indicating pressures. It is capable of indicating positive pressures, that is to say pressures above atmospheric. It is also possible to indicate negative pressures, that is to say pressures which are less than atmospheric. In other words, when there is a negative pressure at the port 22 the diaphragm 50 will be resiliently deformed in a direction towards the port 22. It is possible to modify the arrangement by changing the shape of the base wall 20 in order to accommodate greater degrees of resilient deformation of the diaphragm 50 when subjected to negative pressures.

Figure 24:
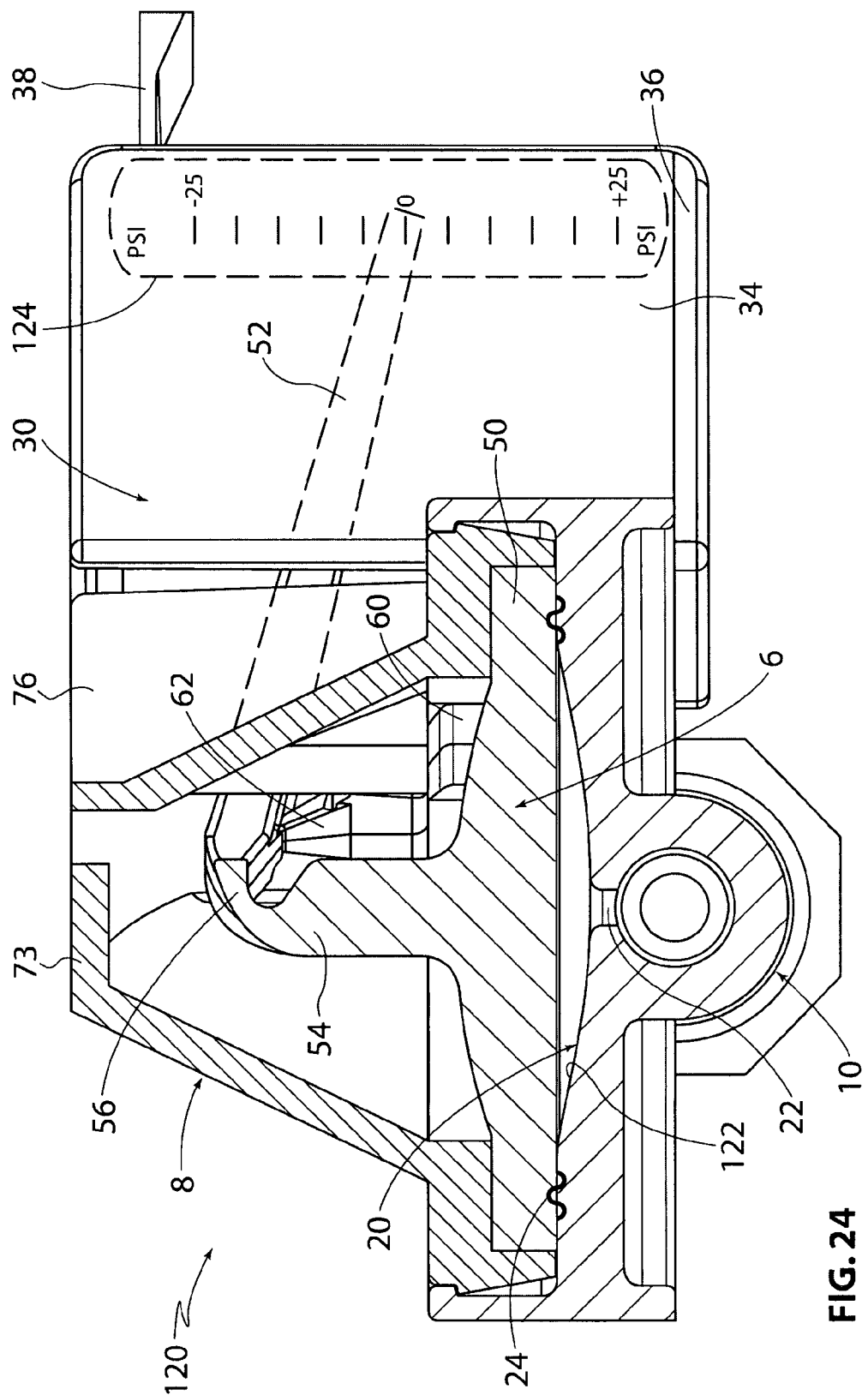
FIG. 24 is an enlarged side view of a modified indicator of the invention.

FIG. 24 illustrates a modified indicator 120 which is modified slightly so that it can indicate positive as well as negative pressures. In this embodiment, the same reference numerals have been used to denote parts which are the same as or correspond to those of the earlier embodiment. More particularly, FIG. 24 corresponds to FIG. 13 of the previous embodiment. It will be seen that the base wall 20 includes a concave dish formation 122 which can permit a greater degree of downward resilient flexure of the diaphragm 50 when the pressure within the port 22 is less than atmospheric. In this embodiment, the indicator arm 52 is arranged so that it occupies a central position within the indicator housing 30 when at rest or subject to zero pressure in the port 22. When positive pressures are applied in the port 22, the diaphragm 50 flexes upwardly so that the indicator arm 52 moves downwardly so as to indicate positive pressures against the scale 124 which is applied to or on the sidewalls 32 or 34 or both of them. When, however, a negative pressure is applied to the port 22, the diaphragm 50 is deflected downwardly so that the indicator arm 52 moves upwardly so as to indicate negative pressures against the scale 124.

As indicated above, the modified indicator 120 is specially designed so that it can readily indicate positive as well as negative pressures. A modification can be readily made to the device shown in FIGS. 1 to 23 so that it is better able to indicate both positive and negative pressures. More particularly, the lower face 126 of the diaphragm 50 can be partially removed, say for instance at broken line 128 shown in FIG. 13. If the disc of material bounded by the broken line 128 were removed this would create a gap between the stepped lower face of the diaphragm 50 and the base wall 20 which would enable a greater degree of downward deflection of the diaphragm 50 and hence the modified device would also be better able to indicate positive as well as negative pressures.

Many modifications will be apparent to those skilled in the art without departing from the spirit and scope of the invention.

LIST OF PARTS pressure indicating device 2
main body 4
diaphragm assembly 6
diaphragm housing 8
conduit 10
inlet 12
outlet 14
cup-shaped body 16
cylindrical wall 18
base wall 20
port 22
annular rib 24
inwardly projecting lip 25
indicator housing 30
sidewalls 32, 34
bottom wall 36
top wall 38
hinge 40
diaphragm 50
indicating arm 52
upstanding post 54
hinge 56
bracket 58
first leg 60
second leg 62
1st and 2nd blind bores 64, 66
annular base 70
frustoconical projection 72
top wall 73
flanges 74, 76
tapered flange 78
rebate 80
laterally extending projection 90, 92
projections 94, 96
inner flanges 100, 102
pins 104, 106
indicator 120
concave dish formation 122
scale 124
lower face 126
broken line 128

The invention claimed is:
1. A pressure indicator, comprising:
a body having a pressure chamber which has an inlet for communication with a fluid:
a resilient diaphragm having a periphery sealed against the body and having a first side thereof exposed to the fluid within the chamber;
an indicating arm having an inner end which is integrally formed with a second side of the diaphragm and an outer end which is adjacent to a scale; and
a fulcrum integrally formed with the diaphragm, which serves to cause rotation of the indicating arm on resilient deformation of the diaphragm,
wherein the pressure indicator is arranged such that pressure of the fluid within the chamber causes resilient deformation of the diaphragm which in turn causes the outer end of the indicating arm to move relative to the scale thereby indicating the pressure of the fluid in the chamber.
2. An indicator as claimed in claim 1, wherein the chamber has an outlet and, in use, said fluid under pressure flows from the inlet to the outlet through the chamber.
3. An indicator as claimed in claim 2, wherein the indicator includes a fulcrum which serves to cause rotation of the indicating arm on resilient deformation of the diaphragm.
4. An indicator as claimed in claim 1, wherein the diaphragm, indicating arm and fulcrum are injection molded from plastics material.
5. An indicator as claimed in claim 4, wherein the indicator includes a diaphragm housing coupled to the body, the diaphragm being arranged to resiliently deflect into the diaphragm housing when the pressure of the fluid increases above atmospheric pressure.
6. An indicator as claimed in claim 5, wherein the diaphragm housing includes formations which interlock with complementary formations on the body and wherein, in use, the periphery of the diaphragm is clamped between the body and the diaphragm housing.
7. An indicator as claimed in claim 6, wherein the fulcrum extends from a mounting point inwardly adjacent to the periphery of the diaphragm.
8. An indicator as claimed in claim 5, wherein the fulcrum extends from a mounting point inwardly adjacent to the periphery of the diaphragm.
9. An indicator as claimed in claim 5, wherein the diaphragm housing includes guide means which engage or are engagable with the fulcrum to limit displacement of the fulcrum when the diaphragm expands.
10. An indicator as claimed in claim 5, further comprising an indicator housing, the outer end of the indicating arm being located within the indicator housing.
11. An indicator as claimed in claim 10, wherein the indicator housing is integrally formed with the body.
12. An indicator as claimed in claim 5, wherein the body has a base wall and wherein said one side of the diaphragm is spaced from the base wall so that the diaphragm can resiliently deflect towards said base wall when the pressure of the fluid decreases below atmospheric pressure.
13. An indicator as claimed in claim 4, wherein the body has a base wall and wherein said first side of the diaphragm is spaced from the base wall so that the diaphragm can resiliently deflect towards said base wall when the pressure of the fluid decreases below atmospheric pressure.

14. An indicator as claimed in claim 13, wherein the fulcrum extends from a mounting point inwardly adjacent to the periphery of the diaphragm.

15. The pressure indicator of claim 1, further comprising:
a diaphragm housing including formations which interlock with complementary formations on the body, wherein the periphery of the diaphragm is configured to be, in use, clamped between the body and the diaphragm housing.

16. The pressure indicator of claim 1, wherein
the pressure chamber has an inlet for communication with a fluid under positive or negative pressure relative to atmosphere.

17. An indicator as claimed in claim 1, wherein the diaphragm is in the form of a disc.

18. An indicator as claimed in claim 17, wherein the disc is circular.

19. An indicator as claimed in claim 1, wherein the diaphragm is substantially flat.

20. A resilient diaphragm for use in a pressure indicator, the resilient diaphragm having a first face and a second face, the first face being configured to be, in use, exposed to a fluid within a chamber, the resilient diaphragm having:
an indicating arm having an inner end which is integrally formed with the second face of the diaphragm and projects from the second face,. and an outer end configured to be located, in use, adjacent to a scale; and
a fulcrum integrally formed with the diaphragm, which serves to cause rotation of the indicating arm on resilient deformation of the diaphragm.

21. A resilient diaphragm for a pressure indicator, the diaphragm having a periphery configured to be, in use, sealed against a body having a pressure chamber therein, and a first face configured to be, in use, subjected to a pressure within the chamber, the diaphragm including:
an indicating arm having an inner end which is integrally formed with a second face of the diaphragm, and an outer end configured to be located, in use, adjacent to a scale; and
a fulcrum integrally formed with the diaphragm, which serves to cause rotation of the indicating arm on resilient deformation of the diaphragm,
wherein said diaphragm is configured such that, in use, pressure within the chamber causes resilient deformation of the diaphragm which in turn causes the outer end of the arm to move relative to the scale thereby indicating the pressure of the fluid in the chamber.

* * * * *